US005861360A

United States Patent [19]

Rademacher et al.

[11] Patent Number: 5,861,360

[45] Date of Patent: Jan. 19, 1999

[54] ENCAPSULATED PLANT GROWTH REGULATOR FORMULATIONS AND APPLICATIONS

[75] Inventors: Wilhelm Rademacher, Limburgerhof, Germany; Charles W. Helpert, Durham; Charles W. Finch, Garner, both of N.C.; Mary Callan, Limburgerhof, Germany; Hans von Amsberg, Chapel Hill, N.C.

[73] Assignee: BASF Corporation, Mount Olive, N.J.

[21] Appl. No.: 771,734

[22] Filed: Dec. 20, 1996

Related U.S. Application Data

[60] Provisional application No. 60/008,993, Dec. 21, 1995.

[51] Int. Cl.[6] .......................... A01N 37/00; A01N 37/02; A01N 37/14; A01N 25/00

[52] U.S. Cl. ....................... 504/319; 504/320; 71/DIG. 1

[58] Field of Search .................................... 504/319, 320; 71/DIG. 1

[56] References Cited

U.S. PATENT DOCUMENTS

| | | | |
|---|---|---|---|
| 3,787,198 | 1/1974 | Hagimoto et al. | 504/134 |
| 3,876,782 | 4/1975 | Kishino et al. | 514/113 |
| 3,894,123 | 7/1975 | Kishino et al. | 558/174 |
| 3,928,586 | 12/1975 | Sledzinski et al. | 514/136 |
| 3,970,728 | 7/1976 | Kishino et al. | 558/185 |
| 4,002,458 | 1/1977 | Hofacker | 71/27 |
| 4,124,227 | 11/1978 | Ruis | 503/224 |
| 4,181,715 | 1/1980 | Kondo et al. | 424/122 |
| 4,217,130 | 8/1980 | Tsurata et al. | 504/287 |
| 4,220,464 | 9/1980 | Martin | 504/312 |
| 4,227,918 | 10/1980 | Hofer et al. | 504/350 |
| 4,277,364 | 7/1981 | Shasha et al. | 56/10.8 |
| 4,344,857 | 8/1982 | Shasha et al. | 504/244 |
| 4,347,372 | 8/1982 | Fory et al. | 548/217 |
| 4,382,813 | 5/1983 | Shasha | 504/220 |
| 4,388,464 | 6/1983 | Kristinsson et al. | 548/136 |
| 4,486,218 | 12/1984 | Reiser et al. | 548/262 |
| 4,531,964 | 7/1985 | Shimano et al. | 548/302 |
| 4,534,783 | 8/1985 | Beestman | 71/27 |
| 4,554,155 | 11/1985 | Allan et al. | 424/419 |
| 4,561,880 | 12/1985 | Shimano et al. | 548/264 |
| 4,563,212 | 1/1986 | Becher et al. | 71/DIG. 1 |
| 4,594,099 | 6/1986 | Yamada et al. | 548/513 |
| 4,640,709 | 2/1987 | Beestman | 71/DIG. 1 |
| 4,647,302 | 3/1987 | Reiser et al. | 514/383 |
| 4,659,722 | 4/1987 | Nakagawa et al. | 514/332 |
| 4,690,934 | 9/1987 | Yoshida et al. | 514/354 |
| 4,715,883 | 12/1987 | Lukaszczyk et al. | 504/106 |
| 4,729,783 | 3/1988 | Regel et al. | 514/383 |
| 4,743,293 | 5/1988 | Reiser et al. | 548/262 |
| 4,744,811 | 5/1988 | Schulz et al. | 504/319 |
| 4,749,405 | 6/1988 | Reiser et al. | 514/184 |
| 4,785,048 | 11/1988 | Chao | 427/146 |
| 4,804,762 | 2/1989 | Yoshida et al. | 514/336 |
| 4,851,035 | 7/1989 | Pirrung et al. | 504/320 |
| 4,871,766 | 10/1989 | Tsuda et al. | 514/521 |
| 4,911,952 | 3/1990 | Doane et al. | 71/DIG. 1 |
| 4,923,503 | 5/1990 | Schulz et al. | 504/274 |
| 4,936,901 | 6/1990 | Surgant et al. | 504/133 |
| 4,952,402 | 8/1990 | Sparks et al. | 424/419 |
| 4,956,129 | 9/1990 | Scher et al. | 264/4.7 |
| 4,997,642 | 3/1991 | Curtis et al. | 424/681 |
| 5,024,937 | 6/1991 | Penticoff et al. | 435/41 |
| 5,037,716 | 8/1991 | Moffat | 430/109 |
| 5,069,711 | 12/1991 | Fischer et al. | 504/246 |
| 5,078,888 | 1/1992 | Penticoff et al. | 210/639 |
| 5,087,456 | 2/1992 | Meinard et al. | 424/501 |
| 5,089,046 | 2/1992 | Lee et al. | 504/207 |
| 5,125,959 | 6/1992 | Suyama et al. | 504/253 |
| 5,126,360 | 6/1992 | Dutzmann et al. | 514/383 |
| 5,130,131 | 7/1992 | Narayanan et al. | 424/94.65 |
| 5,135,942 | 8/1992 | Dutzmann et al. | 514/383 |
| 5,139,774 | 8/1992 | Meinard et al. | 71/DIG. 1 |
| 5,160,529 | 11/1992 | Scher et al. | 71/DIG. 1 |
| 5,221,318 | 6/1993 | Fischer et al. | 504/283 |
| 5,223,526 | 6/1993 | McLoughlin et al. | 514/406 |

(List continued on next page.)

FOREIGN PATENT DOCUMENTS

| | | |
|---|---|---|
| 0 145 846 A2 | 8/1984 | European Pat. Off. . |

OTHER PUBLICATIONS

Abeles; "Abscission: Role of Cellulase"; (1969) 44:447–452; *Plant Physiol.*

Amagasa, et al.; "The Mode of Flower–Inhibiting Action of Ethylene in *Pharbitis nil"*; (1987) 28(6):1159–1161; *Plant Cell Physiol.*

Atsmon, et al; "Comparative effects of gibberellin, silver nitrate and aminoethoxyvinyl glycine on sexual tendency and ethylene evolution in the cucumber plant"; (1979) 20(8):1547–1555; *Plant and Cell Physiol.*

BASF Corporation; "Pix® plant regulator—Results in Cotton (Southwest)"; (1987); *Technical Information Bulletin No. 8626.*

Beyer, et al; "Abscission: The Role of Ethylene Modification of Auxin Transport"; (1971) 48:208–212; *Plant Physiol.*

Cockshull, et al.; "2–Chloroethylphosphonic acid abd flower initiation by *Chrysanthemum morifolium*Ramat, in short days and in long days"; (1978) 53:85–90; *Journal of Horticultural Science.*

Gianfagna, et al; "Mode of action and use of plant growth retardants in reducing the effects of environmental stress on horticultural crops"; (1992) 778–787; *Plant Growth Regulation.*

(List continued on next page.)

*Primary Examiner*—John Pak
*Attorney, Agent, or Firm*—George A. Gilbert

[57] ABSTRACT

Provided herein is a plant growth regulator formulation comprising a plant growth regulator dispersed in polyvinyl alcohol ("PVA") particles having a mean diameter greater than 1 micron. The present invention also includes an emulsion containing an aqueous dispersion of PVA encapsulated plant growth regulator particles wherein said particles have a mean diameter greater than 1 micron. The above formulations are useful in methods of improving a plant growth factor in a plant.

5 Claims, No Drawings

U.S. PATENT DOCUMENTS

| | | | |
|---|---|---|---|
| 5,228,896 | 7/1993 | Misslitz et al. | 504/288 |
| 5,250,505 | 10/1993 | Kast et al. | 504/292 |
| 5,310,721 | 5/1994 | Lo | 504/116 |
| 5,330,965 | 7/1994 | Misslitz et al. | 504/244 |
| 5,332,584 | 7/1994 | Scher et al. | 424/408 |
| 5,364,834 | 11/1994 | Kirchner et al. | 504/319 |
| 5,374,609 | 12/1994 | Kast et al. | 504/344 |
| 5,403,812 | 4/1995 | Kast et al | 504/100 |
| 5,407,896 | 4/1995 | Kast et al. | 504/100 |
| 5,420,148 | 5/1995 | Dehne et al. | 514/395 |
| 5,433,173 | 7/1995 | Markles | 119/231 |
| 5,439,926 | 8/1995 | Dutzmann et al. | 514/383 |
| 5,446,067 | 8/1995 | Benoit et al. | 514/640 |
| 5,464,769 | 11/1995 | Attree et al. | 435/240.4 |
| 5,466,460 | 11/1995 | McMahon et al. | 424/408 |
| 5,705,648 | 1/1998 | Clark et al. | 546/349 |

OTHER PUBLICATIONS

Grossmann, et al; "Inhibition of Ethylene Production in Sunflower Cell Suspensions by a Novel Oxime Ether Derivative"; (1991) 10:163–166; *Journal of Plant Growth Regulation.*

Guinn; "Abscission of Cotton Floral Buds and Bolls as Influenced by Factors Affecting Photosynthesis and Respiration"; (1974) 14:291–293; *Crop Science.*

Guinn; "Effects of Some Organic Solvents on Ethylene Evolution From Young Cotton Bolls"; (1977) 60:446–448; *Plant Physiol.*

Guinn; "Fruit Age and Changes in Abscisic Content, Etylene Production, and Abscission Rate of Cotton Fruits"; (1982) 69:349–353; *Plant Physiol.*

Guinn; "Hormonal Relations in Flowering, Fruiting, and Cutout"; 265–272; *Western Cotton Research Laboratory.*

Guinn; "Nutritional Stress and Ethylene Evolution by Young Cotton Bolls"; (1976) 16:89–91; *Crop Science.*

Hoffmann; "Use of plant growth regulators in arable crops: Survey and outlook"; (1991) 798–808; *Progress in Plant Growth Regulation.*

Kirchner, et al; "Effects of novel oxime ether derivatives of aminooxyacetic acid on ethylene formation in leaves of oilseed rape and barley and on carnation flower senescence"; (1993) 13:41–46; *Plant Growth Regulation.*

Koning; "Control of Flower Opening by Plant Hormones in Gaillardia Grandiflora"; (1981) 40–67; *Dissertation, University of Michigan.*

Lay–Yee, et al.; "Changes in Cotyledon mRNA during Ethylene Inhibition of Floral Induction in *Pharbitis nil* Strain Violet"; (1987) 84:545–548; *Plant Physiol.*

Lipe, et al; "Ethylene, a Regulator of Young Fruit Abscission"; (1973) 51:949–953; *Plant Physiol.*

Lipe, et al; "Ethylene: Role in Fruit Abscission and Dehiscence Processes"; (1972) 50:759–764; *Plant Physiol.*

Machackova, et al; "Reversal of IAA–Induced Inhibition of Flowering by Aminoethoxyvinylglycine in Chenopodium"; (1986) 4:203–209; *Journal of Plant Growth Regulation.*

Owens, et al; "Induction of Perfect Flowers on Gynoecious Muskmelon by Silver Nitrate and Aminoethoxyvinylglycine"; (1980) 15(5):654–655; *HortScience.*

Owens, et al; "Induction of Staminate Flowers on Gynoecious Cucumber by Aminoethoxyvinylglycine"; (1980) 15(3):256–257; *HortScience.*

Stanley, et at.; "The site of ethephon application and its effect on flower initiation and growth of chrysanthemum"; (1989) 64(3)341–350; *Journal of Horticultural Science.*

Suge; "Inhibition of photoperiodic floral induction in *Pharbitis nil* by ethylene"; (1972) 13:1031–1038; *Plant & Cell Physiol.* van Altvorst, et al; "The role of ethylene in the senescence of carnation flowers, a review"; (1995) 16:43–53; *Plant Growth Regulation.* van Doorn, et al; "Developments in the use of growth regulators for the maintenance of post–harvest quality in cut flowers and potted plants"; (1991) 298:195–208; *Acta Horticulturae.*

Veen; "Use of Inhibitors of Ethylene Action"; (1987) 201:213–222; *Acta Horticulturae.*

White, et al; "Environmental control of ethylene biosynthesis"; (1992) 147–155; *Progress in Plant Growth Regulation.*

Woltering, et al; "Amino–oxyacetic acid: analysis and toxicology"; (1987) 216:273–280; *Acta Horticulturae.*

ENCAPSULATED PLANT GROWTH REGULATOR FORMULATIONS AND APPLICATIONS

This application claims the benefit of U.S. Provisional Application No. 60/008,993 filed Dec. 21, 1995.

NOTICE OF COPENDING PATENT APPLICATIONS

The following patent applications are copending in the United States patent and Trademark Office with this application:

1. Plant Growth Retardants In Combination With Inhibitors Of Ethylene Biosynthesis Or Action, U.S. patent application Ser. No. 08/770,788, filed on even date herewith (Dec. 20, 1996), and incorporated herein by reference;
2. Low Rate Application of Inhibitors of Ethylene Biosynthesis or Action, U.S. patent application Ser. No. 08/770,492, filed on even date herewith (Dec. 20, 1996) and incorporated herein by reference;
3. Encapsulated Plant Growth Regulator Formulations, U.S. patent application Ser. No. 08/771,319, filed on even date herewith (Dec. 20, 1996) and incorporated herein by reference;
4. Encapsulated Plant Growth Regulator Formulations In Combination With Plant Growth Retardants, U.S. patent application Ser. No. 08/771,769, filed on even date herewith (Dec. 20, 1996), and incorporated herein by reference;
5. Plant Growth Regulators In Pyrrolidone Solvents, U.S. patent application Ser. No. 08/771,768, filed on even date herewith (Dec. 20, 1996), and incorporated herein by reference;
6. Enhancing The Rate of Seed Germination With Application of Ethylene Biosynthesis Inhibitors, U.S. patent application Ser. No. 08/770,789, filed on even date herewith (Dec. 20, 1996), and incorporated herein by reference; and
7. Aminovinylglycine in combination with a Plant Growth Regulator, U.S. patent application Ser. No. 08/777,716, filed on even date herewith (Dec. 20, 1996), and incorporated herein by reference.

FIELD OF THE INVENTION

The present invention is related generally to the field of agriculture and specifically to compositions and use of plant growth regulators.

BACKGROUND OF THE INVENTION

Agriculture workers actively seek ways to improve the economic output of commercial crops. For example, in cotton crops, workers seek to improve such growth factors as increased boll set, increased floral initiation, decreased floral abscission, decreased boll abscission, increased germination, and enhanced root growth. Workers also seek to increase plant tolerance to environmental stress.

Formulations containing plant growth regulators (PGRs) have been developed to improve the economic yield of agricultural plants. Plant growth retardants and inhibitors of ethylene biosynthesis or action are two types of PGRs. Some plant growth retardants have been shown to inhibit gibberellin biosynthesis resulting in the reduction of shoot height in small grains and cotton. This reduction in shoot height has a strong economic benefit since it provides for less lodging in small grains and reduction of excessive vegetative growth. It also provides more uniform ripening in cotton.

Three groups of gibberellin biosynthesis inhibitors are known. The first group encompasses compounds with quaternary ammonium, phosphonium or sulphonium moieties. One example of a compound from this group is mepiquat chloride, described in U.S. Pat. No. 3,905,798 and incorporated herein by reference. Mepiquat chloride may increase cotton yields, boll load, lint yield and seed yield. Mepiquat chloride is also known to reduce vegetative growth, plant height and boll rot. Mepiquat chloride also induces early uniform ripeness if the plants are treated early during their development. Chloromequat chloride is also a representative compound of this group.

The second group of plant growth retardants encompasses compounds with a nitrogen containing heterocycle such as flurprimidol, paclobutrazol, uniconazole and ancymidol.

The third group encompasses acylcylcohexanediones (such as trinexapac-ethyl and prohexadione-Ca) and daminozide.

It is known that ethylene is involved in plant senescence and plant stress reactions. Ethylene is also involved in leaf, flower, and fruit abscission. Hence, agents that inhibit or regulate the production of ethylene or control its action in plants have been developed in an effort to improve the yield of agricultural crops. Inhibitors of ethylene biosynthesis include substituted oxime-ethers as described in U.S. Pat. No. 4,744,811, incorporated herein by reference. These compounds are also described in PCT Application WO 95-02211, incorporated herein by reference, as being soil amendment compositions that increase the assimilation of nitrogen by higher plants.

Other inhibitors of ethylene biosynthesis or action include aminoethoxyvinylglycine ("AVG"), aminooxyacetic acid ("AOA"), rhizobitoxine, and methoxyvinyl glycine ("MVG"). Silver ions (e.g. silver thiosulfate), and 2,5-norbornadiene inhibit ethylene action.

Plant growth regulators have also been used to protect crops from the effects of environmental stress. Gianfagna, T. J. et al. "Mode of Action and Use of Growth Retardants in Reducing the Effects of Environmental Stress on Horticultural Crops: Karssen C. N. et al. (eds.) *Progress in Plant Growth Regulation*, pp. 778–87 (1992). For example, researchers found that if ethephon was applied at a low rate (0.08 mM) it significantly delayed bloom in peach and reduced side effects. Researchers also found that ethephon increased the yields and hardiness of several horticultural plants.

Although PGRs have been developed as a means to improve agricultural crop yields, certain obstacles make the actual use of the PGR prohibitive. For example, many of the compounds display phytotoxicity. Other compounds are difficult to synthesize.

Many compounds require high rate applications to be effective. For example, PCT Application WO 93/07747, incorporated herein by reference, describes an improvement in a plant growth factor by applying aminoethoxyvinylglycine ("AVG"), an inhibitor of ethylene biosynthesis, to cotton plants. As the rate of AVG treatment increased, so did the improvement. (WO 93/07747, Examples 2–4). Assuming that a spray volume of 500 l/ha was used, the rates of application described in WO 93/07747 would be approximately 62.5 to 500 g ai/ha (ai—active ingredient). The maximum rate response occurs at the highest rates.

High rate applications may result in a significant waste of material and may result in the discharge of the PGRs into the surrounding environment. Also, although many of these compounds may induce a beneficial growth habit, they do not provide consistent improvement in plant growth factors. Other compounds may lose their effectiveness or cause a reduction in yield when applied to species which are under some form of environmental stress.

Encapsulated herbicides, pesticides and plant growth regulators have been described in the prior art. The use of interfacial polymerization to microencapsulate both water-soluble and water-insoluble materials using polymers is known. Others have described entrapped water-insoluble PGRs in starch. U.S. Pat. No. 4,382,813.

Polyvinyl alcohol (PVA) has been described as: a protective colloid in an emulsion formed by the dispersion of an organic solution containing a plant growth regulator, U.S. Pat. No. 5,160,529; as a dispersant in an oil-in-water emulsion, U.S. Pat. No. 4,871,766; as an ingredient in powders, granules or lattices, U.S. Pat. No. 4,486,218; and as an ingredient in oil-in-water emulsions having particles from 1 to 200 microns wherein the emulsion also contains a thickener., U.S. Pat. No. 4,283,415.

U.S. Pat. No. 4,997,642 discloses stable oil-in-water emulsions containing a PVA, a surfactant, a salt, and a water-insoluble oily compound, such as a plant growth regulator, wherein the compound is dispersed as a particle having an average size of less than one micron.

Although these formulations provide unique benefits in the art, obstacles still are encountered by those of ordinary skill in the art in developing formulations containing encapsulated plant growth regulators having a particle size of greater than one micron which are stable, provide for increased improvements in plant growth factors, and that do not need a thickener. Further, many of the prior art formulations do not provide for the slow release of the active ingredient. Obstacles still remain in providing formulations that are not phytotoxic.

Hence, it is an object of this invention to not only provide a stable formulation, but one that also provides for a stable active compound in solution. It is also an object of the invention to provide a slow release formulation that improves a plant growth factor. It is still yet further an object of the present invention to provide a PGR that has lower application rates, has limited environmental impact, and has reduced plant toxicity.

SUMMARY OF THE INVENTION

Provided herein is a plant growth regulator formulation comprising a plant growth regulator dispersed in polyvinyl alcohol ("PVA") particles having a mean diameter greater than 1 micron. The present invention also includes an emulsion containing an aqueous dispersion of PVA encapsulated plant growth regulator particles wherein said particles have a mean diameter greater than 1 micron. Thus, the present invention is directed to a particle comprising a plant growth regulator contained in a polyvinyl alcohol matrix.

The above formulations are useful in methods of improving a plant growth factor in a plant comprising administering to said plant a plant growth regulator formulation comprising the formulations of the present invention, i.e., a plant growth regulator dispersed in polyvinyl alcohol ("PVA") particles having a mean diameter greater than 1 micron. The methods also include applying an emulsion containing an aqueous dispersion of PVA encapsulated plant growth regulator particles wherein said particles have a mean diameter greater than 1 micron.

An improvement in a plant growth factor is defined as an agronomic improvement of plant growth such as increased floral (square) initiation, increased flower retention, increased fruit retention, increased square retention, increased boll retention, increased root growth, decreased internode length, increased stress tolerance, decreased wilting, decreased senescence, darker green pigmentation, increased germination rate, increased tolerance to low and high temperatures, and increased crop yield. That is, a favorable alteration of the physiology or growth of plants or an increase or decrease in plant growth which leads to an economic or agronomic benefit. Improvement in growth factors that result from the inhibition of ethylene production is preferred.

DETAILED DESCRIPTION OF THE INVENTION

The emulsions of the present invention are particularly suitable for formulations containing PVA encapsulated inhibitors of ethylene biosynthesis or action, preferably substituted oxime-ethers having the formula:

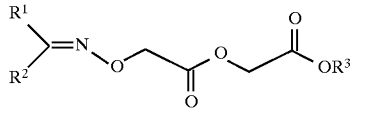
(I)

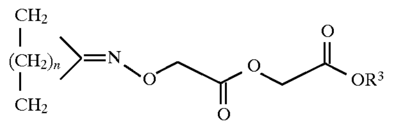
(II)

where R1 and R2 independently of one another are C1–C6-akyl, n is 2 or 3 and R3 is hydrogen or C1–C6 akyl.

Examples of other compounds that may be used include [((isopropylidene)-amino]oxy acetic acid represented by the structure:

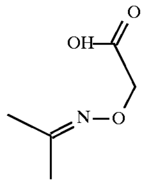
(III)

Another example of a compound that may used in the present invention is aminooxyacetic ("AOA") acid represented by the following structure:

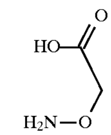
(IV)

Preferred oxime-ethers for use in the formulations include the following compounds:

1) {[(isopropylidene)-amino]oxy}-acetic acid-2-(methoxy)-2-oxoethyl ester represented by the structure:

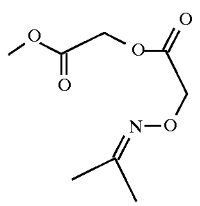
(V)

2) {[(isopropylidene)-amino]oxy}-acetic acid-2-(hexyloxy)-2-oxoethyl ester represented by the structure:

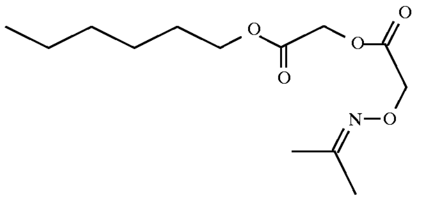

(VI)

and

3) {[cyclohexylidene)-amino]oxy}-acetic acid-2-(isopropyloxy)-2-oxoethyl ester represented by the structure:

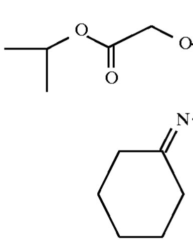

(VII)

The most preferred compound for carrying out the present invention comprises {[(isopropylidene)-amino]oxy}-acetic acid-2-(methoxy)-2-oxoethyl ester.

Other compounds that may be encapsulated according to the invention include aminoethoxyvinylglycine and methoxyvinyl glycine Although water-soluble and water-insoluble compounds may be encapsulated according to the present invention, the preferred compounds for carrying-out the invention are water-insoluble. Compositions of the invention contain, by weight, about 0.1% to about 90% plant growth regulator, about 0.1% to about 30% PVA, about 1% to about 10% buffer, and about 50% to about 99% water. Preferred formulations contain, by weight, about 1% to about 10% plant growth regulator, about 2% to about 8% PVA, about 2% to about 6% buffer with the remaining weight of ingredients containing water and optionally a biocide and a surfactant. The range, by weight, of biocide useful in carrying-out the invention is up to about 25%, preferably from about 0.1 to about 5%. The range of the surfactant is preferably up to about 20%, most preferably from about 2 to about 6%.

The PVA for use in the invention include those having a molecular weight of 15–72K, 44–65K, 70–90K, 44–65K, 7K and 9–13K (K=1,000). The PVA for use in invention also includes those with partial hydrolysis of 87–89% and 78–82%; intermediate hydrolysis of 95.5–96.5%; full hydrolysis of 98–98.8%; and super hydrolysis of greater than 99.3%. Preferred PVA include those with percent hydrolysis greater than 85%.

The most preferred formulation is a plant growth regulator formulation consisting essentially of about 5% of {(isopropylidene)-amino]oxy}-acetic acid-2-(methoxy)-2-oxoethyl ester, about 5% of polyvinyl alcohol, about 0.26% sodium phosphate dibasic and about 90% water. This embodiment of the invention may further include a biocide.

The particles dispersed in the formulations are greater than about one micron and typically have a mean volume diameter of about greater than 1 micron to about 80 microns. Further embodiments of the invention include particles having a size of about greater than one micron to about 50 microns. Another range of particle size useful in practicing the present invention is a particle that has a mean volume diameter greater than about five microns to about 15 microns. A preferred particle size (mean diameter) is about 6 microns to about 10 microns.

The surfactants of this invention include salts of alkyl sulfates, alkyl or aryl sulfonates, dialkylsulfosuccinates, salts of polyoxyethylene alkyl aryl ether, phosphoric acid esters, napththalenesulfonic acid/formaldehyde condensates, polyoxyethylene alkyl ether, polyoxyethylene-polyoxypropylene block copolymers, sorbitan fatty acid esters, or polyoxyethylene sorbitan fatty acid esters, monalkyl quaternary salts, dialkyl quaternary salts, diquaternary salts, ethoxylated monoquaternary salts, ethoxylated diquaternary salts, and lauryl betaine.

An additional release slowing component may be added or dissolved in the water-insoluble plant growth regulator. This component acts to slow the rate of release of the plant growth regulator from the PVA matrix. The preferred release slowing component is polyvinyl acetate having a molecular weight of from about 10K to about 200K.

The formulations are particularly useful as they provide significant improvements in a plant growth factor and are stable, not only against particle aggregation, but the PVA also acts to stabilize the plant growth regulator compound. These formulations provides this benefit in the substantial absence of the following ingredients: 1) a thickener; 2) a surfactant (preferably less than 0.1 weight percent); 3) a salt (preferably less than 1%); 4) a xanthate; 5) a starch; and 6) a hydrocarbon (as described in U.S. Pat. No. 4,871,766).

The formulations of the invention are particularly useful as sustained release formulations. Further benefits are that the formulations provide significant improvement in a plant growth factor and also provide a formulation that has low phytotoxicity.

Preferred formulations of the invention also provide a significant benefit in that they produce a significant improvement in a plant growth factor when applied at low rate. These application rates are described in U.S. Provisional Patent Application No. 60/009,050, entitled "Low Rate Application of Inhibitors of Ethylene Biosynthesis or Action" filed on Dec. 21, 1995. Low rate application is defined as a single application rate lower than about 50 g ai/ha (grams of active ingredient per hectacre). An effective number of low rate applications can be made throughout the growing season. Preferably, the low rate application is performed from one to about ten times during the growing season, most preferably from one to about four times during the growing season. Preferred embodiments of the present invention comprise single application rates ranging from about 100 mg ai/ha to about 50 g ai/ha applied from one to four times during a growing season and ranging from about 500 mg ai/ha to about 10 g ai/ha applied from one to four times during a growing season. Other rates useful for carrying-out the invention include a rate of less than or equal to about 2 g ai/ha and down to about 100 mg ai/ha applied from one to four times during a growing season. The most preferred single application rate is about 500 mg/ha to about 1.5 g ai/ha applied from one to four times during a growing season.

The present invention finds its best results in horticultural and agricultural plants and crops. The invention provides most consistent improvement of at least one plant growth factor in the following plants: cotton, soybean, peanut, pepper, tomato, wheat, barley, rice plant, apple, citrus, grape, corn and canola. Improvement is also found in turf.

The formulations described in this invention are generally applied to the foliage prior to bud and flower development but they can also be applied to the foliage, buds, flowers, or fruits beginning at early bud development (e.g., matchhead square in cotton) in one to four sequential applications. If sequential applications are used, applications are preferably timed at approximately 10 to 14 days apart. When applied by spraying, the active ingredient is generally mixed with water as a carrier solution in a dilution sufficient to cover the area. Typically the spray volume of the aqueous treatment solution would be about 150 to 500 l/ha for arable crops and up to about 1,500 l/ha fruit trees. Soil drenching is another method of application that is useful when practicing the invention.

Accordingly, the present invention provides a method which improves the economic or agronomic output of agricultural crops and decreases the amount of material that needs to be used to obtain improvement in a plant growth factor.

The following examples are illustrative only and are not meant to limit the invention in any manner.

EXPERIMENTS

1. Cotton trials. Field tests with Cotton plants were conducted as follows: Cotton plots were laid out about four rows wide and 30 to 40 feet long. The center two rows of each four row plot were sprayed over the foliage, buds, blooms, and fruits with the respective applications and the outer two rows were not treated in order to provide a buffer row between plots. In most experiments each treatment was replicated four times and organized in randomized complete block design.

The first treatments were applied when the flower buds (i.e., "squares") reached the size of a "match-head", i.e. when the first square of a typical cotton plant was about the size of a matchhead, and when 50% of the plants had one or more matchhead squares. Generally, the formulations, except for the mepiquat chloride, were applied at 1, 10, 20, 50 and 100 g ai/ha. The amount of formulated material to be applied to each treatment was calculated on the basis of the amount of the area to be treated with each rate. For example, a treatment applied at a rate of 1 g of the active ingredient required four applications of 0.022 g ai/ha when four plots (2133 square feet) were treated. Thus, 0.022 g of active material was mixed with one liter of water or the amount of water necessary for the treated area for the spray volume to be equivalent to about 150 to 250 l/ha.

Subsequent to the second and/or final applications the numbers and locations on the plant of the squares, flowers, and bolls were recorded, and when possible, either boll weights or seed cotton yields were obtained.

Greenhouse tests were conducted as follows: Cotton was sown in 2 to 5 liter pots in the greenhouse, approximately one plant per pot, either in field soil or soilless planting mix. Plants remained in the greenhouse, and at the matchhead square stage described in the field methods previously, treatments were applied to the foliage, squares, flowers, and/or bolls either by spraying in a laboratory chamber sprayer (Allen Machine Works, Midland, Mich.), or by placing the pots on the ground outside the greenhouse and spraying with a hand-held spray boom. Spray volumes were approximately equivalent to that described in the field methods. Plants were then returned to the greenhouse and boll counts, boll weights, or seed cotton yields were obtained from the plants.

2. Soybean trials. Soybean trials were conducted in a greenhouse. Soybean seeds were planted in 1000 ml pots in loamy sand soil, fertilized with a slow release fertilizer and allowed to germinate. Plants were thinned to two per pot. When the plants reached the third trifoliate stage, equivalent to 11 true leaves, the plants were treated with the appropriate spray solutions applied over the top of the plants to the foliage.

The plants were placed inside a laboratory spray chamber (e.g. Allen Machine Works, Midland Mich.). As noted above, the foliage was sprayed over the top in order to mimic a typical field application. The plants were returned to the greenhouse. Periodic height measurements, pod numbers, and general plant vigor assessments were conducted. At maturity (approximately six to eight weeks after spraying) the pods were harvested, counted, and the dry-weights recorded.

Control plants were either those completely untreated or those treated with mepiquat chloride (Pix ® plant growth regulator") alone. Mepiquat chloride was applied either alone or in combination with the ethylene biosynthesis inhibitors at a rate of 12 to 200 g ai/ha. When applied in combination, the two compounds were applied using the same "tank-mix" spray solution. However, combinations of mepiquat chloride and ethylene biosynthesis inhibitors may also include separate applications made within 72 hours of each other on the same plants.

EXAMPLE 1

Formulations containing polyvinyl alcohol (PVA) encapsulated {(isopropylidene)-amino]oxy}-acetic acid-2-(methoxy)-2-oxoethyl ester (99% Technical Grade; BASF Corporation) were prepared by first making a 10% solution of PVA in an aqueous solution of sodium phosphate dibasic buffer. Various PVA (Air Products, Inc.) was used having different molecular weights and various degrees of hydrolysis. Table 1 lists the different PVA used.

TABLE 1

| | Polyvinyl Alcohol | |
|---|---|---|
| PVA TYPE | MOLECULAR WEIGHT (K) | DEGREE OF HYDROLYSIS |
| AIRVOL ® 205S | 15–27 | Partial (87–89%) |
| AIRVOL ® 523S | 44–65 | Partial (87–89%) |
| AIRVOL ® 540S | 70–90 | Partial (87–89%) |
| AIRVOL ® 125 | 44–65 | Super (99.3% +) |
| AIRVOL ® 325 | 44–65 | Full (98–98.8%) |
| AIRVOL ® 523S | 44–65 | Partial (87–89%) |
| AIRVOL ® 425 | 44–65 | Intermediate (95.5–96.5%) |
| AIRVOL ® 603 | 7 | Partial (87–82%) |
| AIRVOL ® 203 | 9–13 | Partial (87–89%) |

The pH of the 10% PVA solutions was adjusted to about 4.1. The oxime-ether was mixed into the PVA solution under A high shear until a finely dispersed emulsion was obtained. A biocide (Proxel® GXI biocide) was added to the emulsion and mixed. The solutions were passed once through a high shear Eiger Mini 50 (e.g., a bead mill with an 85% chamber loading of 1 mm glass beads) at 3000 RMP. A milky solution was obtained and passed through a 0.45 micron screen. The formulations prepared contained about 5% substituted oxime-ether, about 5% PVA, about 0.12% biocide, about 0.26% sodium phosphate dibasic and about 89.62% water.

Particle size was measured using an Accusizer Optical Particle Sizer. The particle size measured (mean volume) for each formulation was about ten microns.

The formulations were tested in soybeans at rates of 1, 10 and 20 g ai/ha (greenhouse) and compared to a control and unencapsulated {(isopropylidene)-amino]oxy}-acetic acid-2-(methoxy)-2-oxoethyl ester (99% Technical Grade; BASF Corporation). The results are displayed in Table 2.

TABLE 2

(Soybean)

| | Number of Pods | | |
|---|---|---|---|
| rate kg ai/ha | 0.0010 | 0.010 | 0.020 |
| control | 18.2 | 18.2 | 18.2 |
| tech. grade | 23.2 (127%) | 18.4 (101%) | 21.6 (119%) |
| encap. tech. grade (205s) | 23.2 (127%) | 21.8 (120%) | 21.3 (118%) |
| encap. tech. grade (523s) | 20.4 (112%) | 22.6 (124%) | 23.0 (126%) |
| encap. tech. grade (540s) | 25.8 (142%) | 19.2 (105%) | 19.2 (105%) |

The results establish that at low rates the encapsulated {[(isopropylidene)-amino]oxy}-acetic acid-2-(methoxy)-2-oxoethyl ester significantly and consistently improves the number of pods in the soybean plant.

Yield studies in cotton were also performed using a PVA encapsulated compositions (540S as described above). Thirty-seven trials were carried out generally as described above for cotton field studies. The mean relative yields were calculated as compared to the values obtained for the untreated plants. The results are displayed in Table 3.

TABLE 3

(Cotton)

| | Yield | | | | |
|---|---|---|---|---|---|
| Rate(g/ha) | 0.5 | 1 | 10 | 20 | 50 |
| Relative Yield | 96% | 100% | 105% | 97% | 95% |
| Frequency of Positive Yield | 18% | 43% | 59% | 18% | 25% |

The best yield results (5%) were obtained at the 10 g/ha application rates. Also, the formulation applied at 10 g/ha had the highest frequency of positive results. The yields for the formulations applied at the 0.5, 20 and 50 g/ha rates were less than the untreated plants. The results for the plants treated with 1 g/ha application rates were the same as the results obtained for the untreated plants.

EXAMPLE 2

Encapsulated {[(isopropylidene)-amino]oxy}-acetic acid-2-(methoxy)-2-oxoethyl ester formulations were prepared as in Example 1 and combined with mepiquat chloride and mixed in one liter of water. Two formulations were prepared. The first formulation contained PVA with a molecular weight of 44–66K and partial degree of hydrolysis (87–89%) (AIRVOL® 523 S polyvinyl alcohol). The second formulation contained PVA with a molecular of 70–90k and was partially hydrolyzed (87–89%). Cotton plants were treated as described above. The plants were treated and mepiquat chloride treated plants were used as a comparison (Application rate at about 0.012 kg ai/ha). The number of squares and bolls were measured and the results are displayed in Tables 4–6

TABLE 4

(Cotton)

| | Number of Squares[1] | | | | |
|---|---|---|---|---|---|
| rate (kg ai/ha) | 0.001 | 0.010 | 0.020 | 0.050 | 0.10 |
| mc | 8.3 | 8.3 | 8.3 | 8.3 | 8.3 |
| mc + encap. w/523S | 11.3 (136%) | 10.7 (129%) | 8.7 (105%) | 9.8 (118%) | 8.9 (107%) |
| mc + encap. w/540S | 9.8 (118%) | 10.5 (126%) | 8.2 (99%) | 10.1 (122%) | 7.0 (84%) |

[1]Measured after two of four sequential applications (field test)

mc = mepiquat chloride

TABLE 5

(Cotton)

| | Number of Bolls | | | | |
|---|---|---|---|---|---|
| rate (kg ai/ha) | 0.001 | 0.010 | 0.020 | 0.050 | 0.10 |
| mc[1] | 7.8 | 7.8 | 7.8 | 7.8 | 7.8 |
| mc + encap. w/523 S[1] | 10.0 (128%) | 8.1 (104%) | 7.3 | 7.6 | 9.2 |
| mc + encap. w/540S[1] | 9.9 (127%) | 7.6 (97%) | 9.0 (115%) | 7.3 (94%) | 6.9 (88%) |
| mc[2] | 4.1 | 4.1 | 4.1 | 4.1 | 4.1 |
| mc + encap. w/523S[2] | 5.7 (139%) | 5.3 (129%) | 5.8 (142%) | 6.2 (151%) | 6.4 (156%) |
| mc + encap. w/540S[2] | 6.2 (151%) | 8.3 (202%) | 6.1 (149%) | 6.2 (151%) | 5.9 (144%) |
| mc[3] | 7.2 | 7.2 | 7.2 | 7.2 | 7.2 |
| mc + encap. w/523S[3] | 6.2 (86%) | 7.2 (100%) | 6.5 (90%) | 6.5 (80%) | 6.2 (86%) |
| mc + encap. w/540S[3] | 9.0 (125%) | 7.0 (97%) | 7.8 (94%) | 6.8 (94%) | 7.3 (101%) |
| mc[4] | 3.35 | 3.35 | | 3.35 | |
| mc + encap. w/523S[4] | 3.65 (109%) | 3.90 (116%) | | 3.95 (118%) | |

TABLE 5-continued (Cotton)

| | Number of Bolls | | | | |
|---|---|---|---|---|---|
| rate (kg ai/ha) | 0.001 | 0.010 | 0.020 | 0.050 | 0.10 |
| mc + encap. w/540S[4] | 4.22 (126%) | 3,60 (108%) | | 3.30 (99%) | |

[1]Four applications (field data)
[2]Three applications (field data)
[3]Four applications (field data)
[4]Collected after the second of two sequential applications
mc = mepiquat chloride

TABLE 6

(Cotton)

| | Yield | | | | |
|---|---|---|---|---|---|
| rate (kg ai/ha) | 0.001 | 0.010 | 0.020 | 0.050 | 0.10 |
| mc[1] | 1385 | 1365 | 1365 | 1365 | 1365 |
| mc + 523S[1] | 1669 (122%) | 1252 (92%) | 1290 (94%) | 1138 (83%) | 1252 (92%) |
| mc + 540S[1] | 1024 (75%) | 1290 (94%) | 1328 (97%) | 1138 (83%) | 1100 (81%) |
| mc[2] | 2.18 | 2.18 | 2.18 | 2.18 | 2.18 |
| mc + 523S[2] | 2.87 (131%) | 3.25 (149%) | 2.8 (128% | 2.76 (127%) | 2.82 (129%) |
| mc + 540S[2] | 3.43 (157%) | 3.44 (158%) | 3.57 (164%) | 3.4 (156%) | 3.27 (150%) |

[1]Four applications (field test)
[2]Three applications (field test)
mc = mepiquat chloride Examination of the data in Tables 4–6 confirms that the present invention provides consistent improvement in a plant growth factor at low rates. At the low rate application of 1 g ai/ha, the formulation provides significant improvement (about 10% to about 60%) over the mepiquat chloride treated plants.

Thirty-four additional field trials were conducted using the PVA encapsulated formulations (540S) in combination with mepiquat chloride. The mepiquat chloride was applied, for all trials, at a rate of 12 g/ha. The {[(isopropylidene)-amino]oxy}-acetic acid-2-(methoxy)-2-oxoethyl ester was applied at 0.5 g/ha, 1 g/ha, 10 g/ha, 20 g/ha and 50 g/ha. The results are displayed as a percent in Table 7.

TABLE 7

| | Relative % Yield | | | | |
|---|---|---|---|---|---|
| rate (g/ha) | 0.5 g | 1 g | 10 g | 20 g | 50 g |
| mc (12 g/ha) | 103% | 103% | 103% | 104% | 103% |
| mc + PVA Encap. Forms. | 110% | 105% | 106% | 99% | 90% |
| Frequency of Positive Yields | 64% | 72% | 77% | 56% | 25% |

mc = mepiquat chloride

The results for the plants treated with mepiquat chloride alone had a mean value of 103% when compared to the untreated plants with a frequency of positives of 60% of the untreated. Maximum yield for the combination was at 0.5 g/ha rate. Significant increase was seen with the combination below 20 g/ha.

The formulations were also tested in soybeans at rates of 1, 10 and 20 g ai/ha (greenhouse) and compared to an untreated control. The formulations showed an improvement over the untreated control and were comparable to the plants treated with mepiquat chloride.

Another soybean greenhouse study was repeated with the 540s formulations. Mean yield data was obtained (seed weight) at 1, 10 and 50 g/ha. The data obtained showed a decrease in yield when measured as percent of the untreated plants (26%, 30% and 24% at the 1, 10 and 50 g/ha rates respectively).

EXAMPLE 3

In this experiments 50 to 102 seeds were counted and used for each treatment. {[(isopropylidene)-amino]oxy}-acetic acid-2-(methoxy)-2-oxoethyl ester (99% Technical Grade ("tech."); BASF Corporation) was applied either alone or as an encapsulated formulation as described in Example 1. A treatment solution volume of 10 to 50 ml/kg seed was prepared. The formulations were applied at rates of about 1 to 200 mg ai/kg seed. The seeds were mixed and wet with the treatment solutions in flasks and allowed to absorb the applied solutions.

After the seeds had absorbed most of the treatment solutions, they were placed in germination media. The germination media was placed in growth chambers. The growth media consisted of either a loamy sand or an absorbent foam cores (OASIS® CLEAN START® growing media). The seeds were placed at uniform depth in the media. Growth chamber temperatures were held at approximately 70° F. night/80° F. day (12 h/12 h) for the warm treatments, and approximately 55° F. night/70° F. day (12 h/12 h) for the cool treatments. Emerged seedlings were counted on a regular basis. Radiant energy was provided by fluorescent and incandescent light sources for the daytime period. The results for the cool treatments are listed Table 8.

TABLE 8

| Seed Dressing (Cotton) | | | | | | |
|---|---|---|---|---|---|---|
| | Cotton Emergence | | | | | |
| rate | 1 | 10 | 20 | 50 | 100 | 150 |
| 3 DAT | | | | | | |
| control | 0 | 0 | 0 | 0 | 0 | 0 |
| 205S | 1 | 0 | 1 | 1 | 3 | 1 |
| 523S | 0 | 0 | 0 | 0 | 0 | 0 |
| 540S | 0 | 0 | 0 | 0 | 0 | 0 |
| 5 DAT | | | | | | |
| control | 5 | 5 | 5 | 5 | 5 | 5 |
| 205S | 12 | 21 | 10 | 11 | 15 | 8 |
| 523S | 8 | 5 | 6 | 1 | 3 | 0 |
| 540S | 2 | 0 | 1 | 0 | 0 | 0 |
| 7 DAT | | | | | | |
| control | 35 | 35 | 35 | 35 | 35 | 35 |
| 205S | 46 | 52 | 32 | 46 | 52 | 39 |
| 523S | 37 | 30 | 31 | 21 | 12 | 17 |
| 540 | 27 | 18 | 14 | 7 | 6 | 15 |
| 13 DAT | | | | | | |
| control | 38 | 38 | 38 | 38 | 38 | 38 |
| 205S | 51 | 59 | 40 | 48 | 62 | 48 |
| 523S | 50 | 46 | 42 | 51 | 34 | 40 |
| 540S | 45 | 37 | 44 | 37 | 32 | 37 |

There were no improvements seen with the treatments made under the warm temperature treatments using the PVA encapsulated formulations. However, Table 8 shows an improvement in the rate of germination at cool temperatures. Significant improvement was seen with the 205S formulation at about five days (e.g., about a two-fold increase in germination rate up to a four-fold increase in germination rare).

Seed dressing experiments were performed in a Greenhouse study in peanuts with the same treatments. However no cold treatments were performed. The data indicate an increase in shoot growth of most of the plants that were treated with PVA encapsulated formulations.

EXAMPLE 4

Soybean seeds were planted in loamy sand soil in 1 liter pots in the greenhouse, and thinned to three plants per pot after emergence. When the plants reached about the first trifoliate stage or the early bloom stage, 100 ml of a solution containing the equivalent of 0, 30, or 100 or 300 g ai/ha {[(isopropylidene)-amino]oxy}-acetic acid-2-(methoxy)-2-oxoethyl ester (99% Technical Grade ("tech."); BASF Corporation) (free and encapsulated) was applied directly to the soil around the base of the plants. Plant heights were measured at regular intervals and upon maturity, the plants were harvested for fresh and dry weights of the shoots and the bean pods. The results are displayed in Tables 9 and 10

TABLE 9

| (Soil Drenches in Soybeans) | | | |
|---|---|---|---|
| Fresh Weight of Pods (g) | | | |
| Rate (kg ai/ha) | 0.03 | 0.1 | 0.3 |
| Untreated | 7.6 | 7.8 | 7.6 |
| AIRVOL ® 125 | | | |
| 2-3 Trifoliate | 10.9 (143%) | 9.4 (124%) | 9.0 (118%) |
| Early Bloom | 11.7 (154%) | 10.4 (137%) | 10.8 142%) |
| AIRVOL ® 540 S | | | |
| 2-3 Trifoliate | 12.3 (162%) | 10.9 (143%) | 11.5 (151%) |
| Early Bloom | 12.2 (161%) | 12.4 (163%) | 12.7 (167%) |
| AIRVOL ® 205 S | | | |
| 2-3 Trifoliate | 12.3 (162%) | 9.6 (126%) | 12.6 (166%) |
| Early Bloom | 19.5 (138%) | 11.9 (157%) | 11.6 (153%) |
| AIRVOL ® 325 S | | | |
| 2-3 Trifoliate | 10.1 (133%) | 12.4 (163%) | 13.2 (174%) |
| Early Bloom | 11.5 (153%) | 11.8 (155%) | 11.6 (153%) |
| AIRVOL ® 523 S | | | |
| 2-3 Trifoliate | 12.2 (161%) | 12.8 (168%) | 12.8 (168%) |
| Early Bloom | 12.0 (158%) | 13.2 (i74%) | 11.6 (153%) |
| AIRVOL ® 425 | | | |
| 2-3 Trifoliate | 13.7 (180%) | 11.6 (153%) | 11.9 (157%) |
| Early Bloom | 12.0 (158%) | 12.4 (163%) | 10.5 (138%) |

TABLE 10

| (Soil Drenches in Soybeans) | | | |
|---|---|---|---|
| Dry Weight of Pods (g) | | | |
| Rate (kg ai/ha) | 0.03 | 0.1 | 0.3 |
| Untreated | 3.1 | 3.1 | 3.1 |
| AIRVOL ® 125 | | | |
| 2-3 Trifoliate | 5.6 (187%) | 5.0 (161%) | 5.0 (161%) |
| Early Bloom | 6.8 (219%) | 6.5 (210%) | 5.7 (184%) |
| AIRVOL ® 540 S | | | |
| 2-3 Trifoliate | 7.1 (229%) | 6.3 (203%) | 6.7 (216%) |
| Early Bloom | 6.7 (216%) | 6.8 (219%) | 7.0 (226%) |
| AIRVOL ® 205 S | | | |
| 2-3 Trifoliate | 6.7 (216%) | 5.4 (174%) | 6.9 (226%) |
| Early Bloom | 5.6 (181%) | 5.3 (171%) | 5.8 (187%) |
| AIRVOL ® 325 S | | | |
| 2-3 Trifoliate | 5.2 (168%) | 6.8 (219%) | 7.1 (229%) |
| Early Bloom | 5.5 (177%) | 6.1 (197%) | 6.5 (210%) |
| AIRVOL ® 523 S | | | |
| 2-3 Trifoliate | 6.8 (219%) | 6.8 (219%) | 6.8 (219%) |
| Early Bloom | 6.9 (223%) | 7.2 (232%) | 6.4 (206%) |
| AIRVOL ® 425 | | | |
| 2-3 Trifoliate | 7.3 (235%) | 6.0 (194%) | 6.8 (219%) |
| Early Bloom | 6.7 (216%) | 6.3 (203%) | 5.5 (177%) |

The data show that the plants treated with the encapsulated formulations display a significant increase in the weight of the pods.

EXAMPLE 5

A greenhouse trial was conducted in cotton plants (cv. Delta Pine 50). Single plants were raised on a peat-based substrate in 5 liter containers. Water and nutrients were applied uniformly as needed. The plants were leaf-treated with aqueous sprays of PVA encapsulated {[(isopropylidene)-amino]oxy}-acetic acid-2-(methoxy)-2-oxoethyl ester (540S) in combination with mepiquat chloride the plants were treated at growth stage 61 (beginning of flowering) using approximately 500 l/ha of liquid. The plants were also treated with mepiquat chloride alone. For all studies, mepiquat chloride was applied at rates of 10 and 100 g/ha. The {[(isopropylidene)-amino]oxy}-acetic acid-2-(methoxy)-2-oxoethyl ester was applied at rates of 10 and 100 g/ha. Two days after treatment a one week drought stress was imposed onto part of the plants by reducing water supply to approximately 30% of the regular dosage. The leaves of the plants were thus permanently wilted but not killed. Bolls were harvested fresh when the old ones of the control plants had reached their final size. The shoot length, the number of bolls per plant and the fresh weight of bolls per plant were assessed and calculated. The results did not show consistent improvement over the untreated. Although some improvement was observed over untreated and mepiquat treated plants, there was also observed decreases in the shoot length and the number of bolls at both rates.

For the shoot length measurements, the results of the combination were from 84% to 93% (measured as a % of the untreated). In the drought stressed treated plants the results for the combination ranged from 93% to 99% of the untreated. The results for the 540S formulations was 100% of the untreated at 10 g/ha and 103% of the untreated at 100 g/ha (108% and 97% at the 10 g/ha and 100 g/ha, respectively, for the drought stressed plants). The plants treated with mepiquat chloride alone showed a decrease in shoot length, 95% of the untreated at 10 g/ha and 85% of the untreated at 100 g/ha (97% and 96% for the water stressed plants.

The number of bolls ranged from 84% to 102% of the untreated, for the plants treated with the combination (94% to 100% for the drought stressed plants, respectively). The number of bolls for the 540S treated plants was 100% of the untreated at the 10 g/ha and 97% of the untreated at 100 g/ha (106% and 103% for the drought stressed plants). The results for the plants treated with mepiquat chloride alone was 92% of the untreated for the plants treated at 10 g/ha and 87% of the untreated at 100 g/ha (102% and 95% for the drought stressed plants respectively).

The fresh weight bolls per plant was measured and ranged from 89% to 95% of the untreated for the plants treated with the combination (87% to 101% for the drought stressed plants respectively). The results for the 540S treated plants were 97% of the untreated at the 10 g/ha rate and 91% of the untreated at the 100 g/ha (96% and 103% for the drought stressed plants). The results for the plants treated with mepiquat chloride alone were 95% for the untreated at 10 g/ha and 87% of the untreated at 100 g/ha (96% and 113% for the drought stressed plants respectively).

EXAMPLE 6

Dryland (non-irrigated) winter wheat was grown in the field. PVA encapsulated {[(isopropylidene)-amino]oxy}-acetic acid-2-(methoxy)-2-oxoethyl ester, prepared as described in Example 2 (540S), was applied as a foliar treatments in wheat at 1, 10, 20, and 50 g ai/ha rates, beginning at elongation and continuing every 14 days thereafter for four sequential applications. The trials were conducted in a randomized complete block design, plots 10'× 40', replicated 4 times. The compositions were applied with a flat boom backpack $CO_2$ sprayer, 20 GPA, in an aqueous carrier. Upon maturity, the wheat grain was harvested with a plot combine and the grain yield was recorded. The mean values of yield of the treated plants as compared to the values obtained for the untreated plants was recorded and the data is displayed in Table 11.

TABLE II (Wheat)

| Rate | 1 g ai/ha | 10 g ai/ha | 20 g ai/ha | 50 g ai/ha |
|---|---|---|---|---|
| Yield | 110% | 107% | 113% | 111% |

(Rates expressed as per application, each application a total of 4 times)

The results show an improvements in yield up to 13% of the untreated control. However, the results were non-significant at p=0.05.

EXAMPLE 7

Cherry tomatoes were grown in a greenhouse in large pots and treated with foliar spray applications (20 GPA) of PVA encapsulated [(isopropylidene)-amino]oxy}-acetic acid-2-(methoxy)-2-oxoethyl ester, prepared as described in Example 2 (540S). The plants were treated when the 3rd cluster of fruit (youngest at the time of application) was in the small bud stage. First and second clusters were blooming. Foliar applications were of 1, 3, 10, 30, and 100 g/ha rates in aqueous solutions. The fruits were harvested at maturity, counted, and the fresh weights were recorded and compared to the untreated plants. The results, relative to the untreated plants, are displayed in Table 12.

TABLE 12

(Tomatoes)

| Rate | 1 g | 3 g | 10 g | 30 g | 100 g |
|---|---|---|---|---|---|
| 3rd Cluster Yield | 97% | 121% | 105% | 85% | 85% |
| # of Fruit | 127% | 110% | 103% | 111% | 79% |
| 2nd Cluster Yield | 89% | 109% | 109% | 93% | 90% |
| # of Fruit | 92% | 96% | 98% | 91% | 95% |
| 1st Cluster Yield | 101% | 86% | 90% | 94% | 98% |
| # of Fruit | 97% | 82% | 100% | 100% | 105% |

Improvement of fresh weight was obtained at 3 and 10 g ai/ha in the 2nd and 3rd clusters, and the number of fruits improved in the 1st cluster (30–100 g/ha) and the 3rd cluster (1 g/ha). Best results were achieved with foliar application to the young bud stage at rates of equal to or less than 10 g ai/ha. A similar trial conducted in the greenhouse on beefsteak tomatoes resulted in no improvement in fruit yields or fruit numbers.

EXAMPLE 8

[(isopropylidene)-amino]oxy}-acetic acid-2-(methoxy)-2-oxoethyl ester (Technical grade BASF Corporation) was applied as a foliar spray application to pepper plants (bud stage) grown in the greenhouse. Aqueous solutions of {[(isopropylidene)-amino]oxy}-acetic acid-2-(methoxy)-2-oxoethyl ester was applied at rates of 1, 3, 10, 30 and 100 g ai/ha rates. The fruit was harvested upon maturity, counted, and fresh weights recorded. The results were calculated as percent of the untreated plants and they are displayed in Table 13.

TABLE 13

| Rate (g/ha) | 1 | 3 | 10 | 30 | 100 |
|---|---|---|---|---|---|
| # Fruit | 121% | 115% | 124% | 112% | 117% |
| Yield | 118% | 110% | 123% | 107% | 95% |

Improvements of both fruit numbers and fresh weight yields were obtained, particularly at rates of 10 g ai/ha and below (not significant at p=0.05).

EXAMPLE 9

[(isopropylidene)-amino]oxy}-acetic acid-2-(methoxy)-2-oxoethyl ester (99% Technical Grade, BASF) and encapsulated formulations (205S, 523S, and 540S formulations), prepared as described under Example 2, were applied in 4–6 sequential foliar applications in three small-plot field trials on established turf grass (fescue, bluegrass, and zoysia turfs). Experiments were conducted in a randomized complete block with 4 replications. The treatments were applied as a foliar spray application with a spray volume of approximately 40 gallons per acre in an aqueous dilution at rates of 1, 5, 10, and 20 g ai/ha per application. After the final application, two 2-inch soil cores were taken from the first replication of each trial. The cores were washed and visually evaluated for increases in root mass. Visually obvious increases in root mass were noted in fescue in the 523S and 540S formulation treatments, in bluegrass with the technical grade (10 g and lower), and in zoysia (technical grade below 10 g/ha and the 523S formulations at all rates).

Further controlled studies were conducted in greenhouse on bentgrass and bermudagrass that had been established and mowed several times in 4 inch pots. The study was replicated 7 times. The 523S PVA formulation was applied at 1, 5, 10 and 20 g ai/ha. In one treatment method, the compound was applied in an aqueous foliar spray 24 hours prior to cutting and transplanting from the original container. In the second treatment method, the turf was cut and transplanted and then sprayed with an aqueous foliar application. In a third treatment method, the turf was cut and transplanted and treated with a 50 ml volume of aqueous solution with equivalent active ingredient as that applied in the spray applications. The transplanted turf was removed from the pots, washed, and visual observations were made. Root and shoot dry weights and root lengths measured were measured. The results for bentgrass are displayed in Table 14.

TABLE 14

| Rate (g/ha) | 1 g | 5 | 10 | 20 |
|---|---|---|---|---|
| Root Dry Wt. | 205% | 331%* | 131% | 280%* |
| Root Length | 134% | 153%* | 144%* | 123% |
| Shoot Dry Wt. | 149%* | 129%* | 115% | 145%* |

All values relative to control treated with equivalent amount of water.
*denotes significance at p = 0.05.

The data show a significant increase (p=0.05) in root dry weight and length and shoot dry weight in bentgrass when the drench method is used. The data also show a significant increase in root dry weight and length in bermudagrass with the drench application (20 g ai/ha), and increase in root dry weight with application prior to cutting (1 g ai/ha). For example, the shoot dry weight of the treated turf showed an increase over the untreated of 49%, 29%, 15% and 45% at the 1, 5, 10 and 20 g/ha rates of applications.

EXAMPLE 10

Ethylene inhibition was determined in barely leaves treated with {[(isopropylidene)-amino]oxy}-acetic acid-2-(methoxy)-2-oxoethyl ester (99% Technical Grade ("tech."); BASF Corporation) (both encapsulated and free) using various formulations as described in Example 1. The formulations were applied to seven-day-old greenhouse grown barley leaves at rates of 30 g ai/ha and 300 g ai/ha. The treatments were carried out in a spray chamber at 750 l/has in aqueous solutions made with 0.1M potassium phosphate buffer. The leaves were wilted for one hour and incubated in a gas-tight 55 ml vial for 150 minutes. A one ml gas sample was taken through the septum and analyzed for ethylene content using a gas chromatograph on a $Al_2O_3$ column. The results are shown in Table 15

TABLE 15

| | (Barley Leaves) Ethylene Inhibition (%) | |
|---|---|---|
| Composition | 30 g ai/ha | 300 g ai/ha |
| tech. | 0.0% | 25.0% |
| 540S | 25.0% | 44.2% |
| 523S | 41.7% | 35.8% |
| 205S | 39.2% | 29.2% |

The data in Table 15 show significant inhibition of ethylene production at 30 and 300 g ai/ha. The data further demonstrate that at a ten-fold decrease in application rate, the encapsulated formulation significantly inhibited the production of ethylene whereas the unencapsulated formulation showed no improvement.

EXAMPLE 11

Encapsulated {[((isopropylidene)-amino]oxy}-acectic acid-2-(methoxy)-2-oxoethyl ester was prepared as in Example 1 (540S). Carnation Flowers ("Rosa von Selecta Clem") were used which had been raised under greenhouse conditions by a commercial grower. At harvest, the flower buds had just opened (petals approximately 3 cm longer than the calyx).

A pulse treatment for 24 hours was given to the flowers immediately after harvest by placing the cut ends of the stems into a test solution prepared wth dimineralized water. The flower were treated with the 540S formulations or the {[((isopropylidene)-amino]oxy}-acectic acid-2-(methoxy)-2-oxoethyl ester (99% Technical Grade, BASF Corporation). At the end of the treatment the test solution was replaced by demineralized water.

Treatment and further keeping of the flowers was done under a 16 hour photoperiod under diffuse incandescent light (ca. 6,000 lux).

The results obtained 16 days are after treatment (DAT) display the number of flowers sensed and are listed in Table 16.

TABLE 16

| Sample | Dosage (ppm) | Senescense |
|---|---|---|
| Control (water) | | 8.9 |
| Technical Grade | 100 | 5.3 |
| 540S | 100 | 3.0 |

The data indicate that the 540S formulation provides more than a two-old and up to a three-fold increase in senesence when compared to the control.

The invention has been described with reference to various specific embodiments. However, many variations and modifications may be made while remaining within the scope and spirit of the invention.

We claim:

1. A method of improving yield in a plant comprising administering to said plant an emulsion comprising an aqueous dispersion of polyvinyl alcohol encapsulated plant growth regulator particles wherein said particles have a mean volume diameter of greater than about 1 micron to about 80 microns and said emulsion is provided in the substantial absence of a salt and in the substantial absence of a thickener, and wherein the plant growth regulator comprises a substituted oxime-ether of the formula:

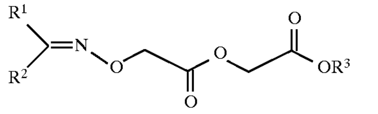
(I)

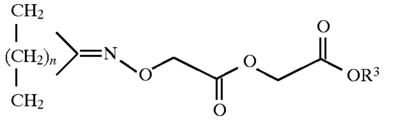
(II)

where $R^1$ and $R^2$ independent of one another are $C_1$ to $C_6$ alkyl, n is 2 or 3 and $R^3$ is hydrogen or $C_1$ to $C_6$ alkyl.

2. The method of claim 1, wherein the substituted oxime-ether is selected from the group consisting of {[(isopropylidene)amino]oxy}-acetic acid-2-(methoxy)-2-oxoethyl ester, {[(isopropylidene)amino]oxy}-acetic acid-2-(hexyloxy)-2-oxoethyl ester, and {[(cyclohexylidene) amino]oxy }-acetic acid-2-(isopropyloxy)-2-oxoethyl ester.

3. The method of claim 1, wherein the substituted oxime-ether comprises {[(isopropylidene)-amino]oxy}-acetic acid-2-(methoxy)-2-oxoethyl ester.

4. A method of improving yield in a plant comprising administering to said plant an emulsion comprising an aqueous dispersion of polyvinyl alcohol encapsulated plant growth regulator particles wherein said particles have a mean volume diameter of greater than about 1 micron to about 80 microns and said emulsion is provided in the substantial absence of a salt and in the substantial absence of a thickener, and wherein the plant growth regulator is selected from the group consisting of {[(isopropylidene) amino]oxy}-acetic acid and aminooxyacetic acid.

5. A method of improving yield in a plant comprising administering to said plant an emulsion comprising an aqueous dispersion of polyvinyl alcohol encapsulated plant growth regulator particles wherein said particles have a mean volume diameter of greater than about 1 micron to about 80 microns and said emulsion is provided in the substantial absence of a salt and in the substantial absence of a thickener, and wherein the plant growth regulator is selected from the group consisting of aminoethoxyvinylglycine and methoxyvinylglycine.

* * * * *